US011096898B2

(12) United States Patent
Basta et al.

(10) Patent No.: US 11,096,898 B2
(45) Date of Patent: Aug. 24, 2021

(54) ALGINATE MICROCAPSULES FOR CELL AND MOLECULAR THERAPY THAT SECRETE BIOACTIVE IMMUNE MOLECULES

(71) Applicant: GH Care Inc., Dix Hills, NY (US)

(72) Inventors: Giuseppe Pietro Pio Basta, Perugia (IT); Pia Montanucci, Bastia Umbra (IT); Riccardo Calafiore, Perugia (IT)

(73) Assignee: GH CARE INC., Dix Hills, NY (US)

( * ) Notice: Subject to any disclaimer, the term of this patent is extended or adjusted under 35 U.S.C. 154(b) by 0 days.

(21) Appl. No.: 16/670,152

(22) Filed: Oct. 31, 2019

(65) Prior Publication Data

US 2020/0155468 A1 May 21, 2020

Related U.S. Application Data

(60) Provisional application No. 62/768,249, filed on Nov. 16, 2018.

(51) Int. Cl.
*A61K 9/50* (2006.01)

(52) U.S. Cl.
CPC .......... *A61K 9/5031* (2013.01); *A61K 9/5036* (2013.01); *A61K 9/5078* (2013.01); *A61K 9/5089* (2013.01)

(58) Field of Classification Search
CPC ................................... A61K 9/5031
See application file for complete search history.

(56) References Cited

U.S. PATENT DOCUMENTS

| 4,663,286 A | 5/1987 | Tsang et al. | |
| 5,876,742 A * | 3/1999 | Cochrum | A01N 1/02 264/4.1 |
| 9,839,615 B2 | 12/2017 | Calafiore et al. | |
| 2009/0214660 A1 * | 8/2009 | Vasconcellos | A61P 1/16 424/490 |
| 2011/0250280 A1 * | 10/2011 | Calafiore | A61P 3/10 424/490 |
| 2014/0105974 A1 * | 4/2014 | Weber | A61K 9/4891 424/463 |
| 2015/0290141 A1 * | 10/2015 | Calafiore | A61K 35/51 424/493 |

FOREIGN PATENT DOCUMENTS

| CN | 106860422 A | 6/2017 | |
| WO | WO-9847948 A1 * | 10/1998 | ............. A61L 27/34 |
| WO | 2007-046719 A2 | 4/2007 | |

OTHER PUBLICATIONS

C. G. Thanos et al. "Formulating the alginate-polyornithine biocapsule for prolonged stability: Evaluation of composition and manufacturing technique." Journal of Biomedical Materials Research Part A, vol. 83A, 2007, pp. 216-224. (Year: 2010).*

Pia Montanucci, Ilaria Pennoni, Teresa Pescara, Paolo Blasi, Giovanni Bistoni, Giuseppe Basta, Riccardo Calafiore. "The functional performance of microencapsulated human pancreatic islet-derived precursor cells." Biomaterials 32 (2011), pp. 9254-9262. (Year: 2011).*

Dinesh B. Shenoy, Gleb B. Sukhorukov. "Microgel-Based Engineered Nanostructures and Their Applicability with Template-Directed Layer-by-Layer Polyelectrolyte Assembly in Protein Encapsulation." Macromolecular Bioscience, vol. 5, 2005, pp. 451-458. (Year: 2005).*

Omaditya Khanna, Monica L. Moya, Emmanuel C. Opara, Eric M. Brey. Synthesis of multilayered alginate microcapsules for the sustained release of fibroblast growth factor-1 Journal of Biomedical Materials Research Part A, vol. 95A, Nov. 2010, pp. 632-640. (Year: 2010).*

Board of Patent Appeals and Interferences. Ex parte Rolf Bergman et al. U.S. Appl. No. 11/470,988, Appeal Docketing No. 2011-013450, published Feb. 1, 2012, pp. 1-20. (Year: 2012).*

CG Thanos et al. "Formulating the alginate-polyornithine biocapsule for prolonged stability: Evaluation of composition and manufacturing technique." Journal of Biomedical Materials Research Part A, vol. 83A, 2007, pp. 216-224. (Year: 2007).*

Riccardo Calafiore. "Alginate microcapsules for pancreatic islet cell graft immunoprotection: struggle and progress towards the final cure for type 1 diabetes mellitus." Expert Opinion in Biological Therapeutics, vol. 3(2), 2003, pp. 201-205. (Year: 2003).*

Darrabie, M.M. et al., "Characteristics of Poly-L-Ornithine-coated alginate microcapsules" Biomaterials (Dec. 2005) pp. 6847-6850, vol. 26, abstract only.

Pareta, R. et al., "Long-Term Function of Islets Encapsulated in a Redesigned Alginate Microcapsule Construct in Omentum Pouches of Immune-Competent Diabetic rats" Pancreas (May 2014) pp. 605-613, vol. 43, No. 4.

International Search Report and Written Opinion issued in International Application No. PCT/US2019/059382, dated Apr. 9, 2020, pp. 1-9.

Wenk, G.L. et al., "A nitride-donating flurbiprofen derivative reduces neuroinflammation without interacting with galantamine in the rat" European Journal of Pharmacology (Sep. 2002) pp. 319-324, vol. 453.

Nocentini, G. et al., "Glucocorticoid-induced tumor necrosis factor receptor-related (GITR)-Fc fusion protein inhibits GITR triggering and protects from the inflammatory response after spinal cord injury" Molecular Pharmacology (Mar. 2008) pp. 1610-1612, vol. 73, No. 6.

Mert Selimoglu, S. et al., "Alginate as an immobilization material for MAb production via encapsulated hybridoma cells" Critical Reviews in Biotechnology (Jun. 2010) pp. 145-159, vol. 30.

(Continued)

*Primary Examiner* — Isaac Shomer

(74) *Attorney, Agent, or Firm* — Tutunjian & Bitetto, P.C.

(57) ABSTRACT

A membrane including a barrier having layers of alginate with different material molar concentrations relative to another material. The layers have a uniform consistency across a thickness of the layers. The thickness is free of laminae and interfaces and forms a single layer morphology that provides permeability for selected molecules.

13 Claims, 7 Drawing Sheets

(56) References Cited

OTHER PUBLICATIONS

Calafiore, R. et al., "Standard technical procedures for microencapsulation of human islets for graft into non immunosuppressed patients with type 1 diabetes mellitus" Transplantation Proceedings (May 2006) pp. 115-1157, vol. 38, No. 4.
Draget, K. I. et al., "Alginates from algae" Polysaccharides and Polyamides in the Food Industry. Properties, Production and Patents (Jan. 2005) pp. 1-30.
Smidsrød, O. et al., "Dependence upon uronic acid composition of some ion-exchange properties of alginates" Acta Chemica Scandinavica (Jan. 1968) pp. 1987-1997, vol. 22, No. 6.
Smidsrød, O., "Solution properties of alginate" Carbohydrate Research (Jan. 1970) pp. 359-372, vol. 13, No. 3.
Smidsrød, O., "Molecular basis for some physical properties of alginates in the gel state" Journal of the Chemical Society (Jan. 1974) pp. 263-274, vol. 57.
Smidsrød, O. et al., "Selectively of some anionic polymers for divalent metal ions" Acta Chemica Scandinavica (Jan. 1970) pp. 843-854, vol. 24, No. 3.
Montanucci, P. et al., "Insights in Behavior of Variably Formulated Alginate-Based Microcapsules for Cell Transplantation" Hindawi Publishing Corporation BioMed Research International (Sep. 2014) pp. 1-12, Article ID 965804.
Calafiore, R. et al., "Clinical application of microencapsulated islets: Actual prospectives on progress and challenges" Advanced Drug Delivery Reviews Nov. 2013) pp. 84-92, vol. 67-68.
Basta, G. et al., "Long-term metabolic and immunological follow-up of nonimmunosuppressed patients with type 1 diabetes treated with microencapsulated islet allografts: four cases" Diabetes Care (Nov. 2011) pp. 2406-2409, vol. 34, No. 11.
Montanucci, P. et al., "The functional performance of microencapsulated human pancreatic islet derived precursor cells" Biomaterials (Sep. 2011) pp. 9254-9262, vol. 32, No. 35.
Montanucci, P. et al., "Restoration of t cell substes of patients with type 1 diabetes mellitus by microencapsulated human umbilical cord Wharton jelly-derived mesenchymal stem cells: An in vitro study" Clinical Immunology (Feb. 2016) pp. 34-41, vol. 163.
Montanucci, P. et al., "Treatment of diabetes mellitus with microencapsulated fetal human liver (FH-B-TPN) engineered cells" Biomaterials (Feb. 2013) pp. 4002-4012, vol. 34, No. 16.
Nishioka, T. et al., "In vivo expansion of CD4+Foxp3+ regulatory T cells mediated by GITR molecules" Immunol Letters Oct. 2008) pp. 97-104, vol. 121, No. 2.
Gonzalez-Pujana, A. et al., "Alginate Microcapsules for Drug Delivery" Alginates and Their Biomedical Applications (Nov. 2017) pp. 67-100, abstract only.
Acarregui, A. et al., "Hydrogel-Based Scaffolds for Enclosing Encapsulated Therapeutic Cells" Biomacromolecules (Jan. 2013) pp. 322-330, vol. 14, No. 2.
Emerich, D.F. et al., "Encapsulated cell therapy for neurodegenerative diseases: From promise to product" Advanced Drug Delivery Reviews (Apr. 2014) pp. 131-141, vol. 67-68.
Grandoso, L. et al., "Long-term survival of encapsulated GDNF secreting cells implanted within the striatum of parkinsonized rats" International Journal of Pharmaceutics (May 2007) pp. 69-78, vol. 343.
Spuch, C. et al., "The effect of encapsulated VEGF-secreting cells on brain amyloid load and behavioral impairment in a mouse model of Alzheimer's disease" Biomaterials (Apr. 2010) pp. 5608-5618, vol. 31.
Read, T.A. et al., "Local endostatin treatment of gliomas administered by microencapsulated producer cells" Nature Biotechnology (Jan. 2001) pp. 29-34, vol. 19, No. 1.
Alunno, A. et al., "In vitro immunomodulatory effects of microencapsulated umbilical cord Wharton jelly-derived mesenchymal stem cells in primary Sjögren's syndrome" Rheumatology (Jan. 2015) pp. 163-168, vol. 54, No. 1.
Dubrot, J. et al., "Delivery of immunostimulatory monoclonal antibodies by encapsulated hybridoma cells" Cancer Immunol Immunother (Nov. 2010) pp. 1621-1631, vol. 59, No. 11.
Saenz del Burgo, L. et al., "Microencapsulation of therapeutic bispecific antibodies producing cells: immunotherapeutic organoids for cancer management" Journal of Drug Targeting (Feb. 2015) pp. 1-10, vol. 23, No. 2.
Saenz del Burgo, L. et al., "Microencapsulated Cells for Cancer Therapy" Methods Mol Biol. (Jan. 2017) pp. 261-272, vol. 14.
Orive, G. et al., "Cell encapsulation: technical and clinical advances" Trends Pharmacol Sci. (Aug. 2015) pp. 537-546, vol. 36, No. 8.

* cited by examiner

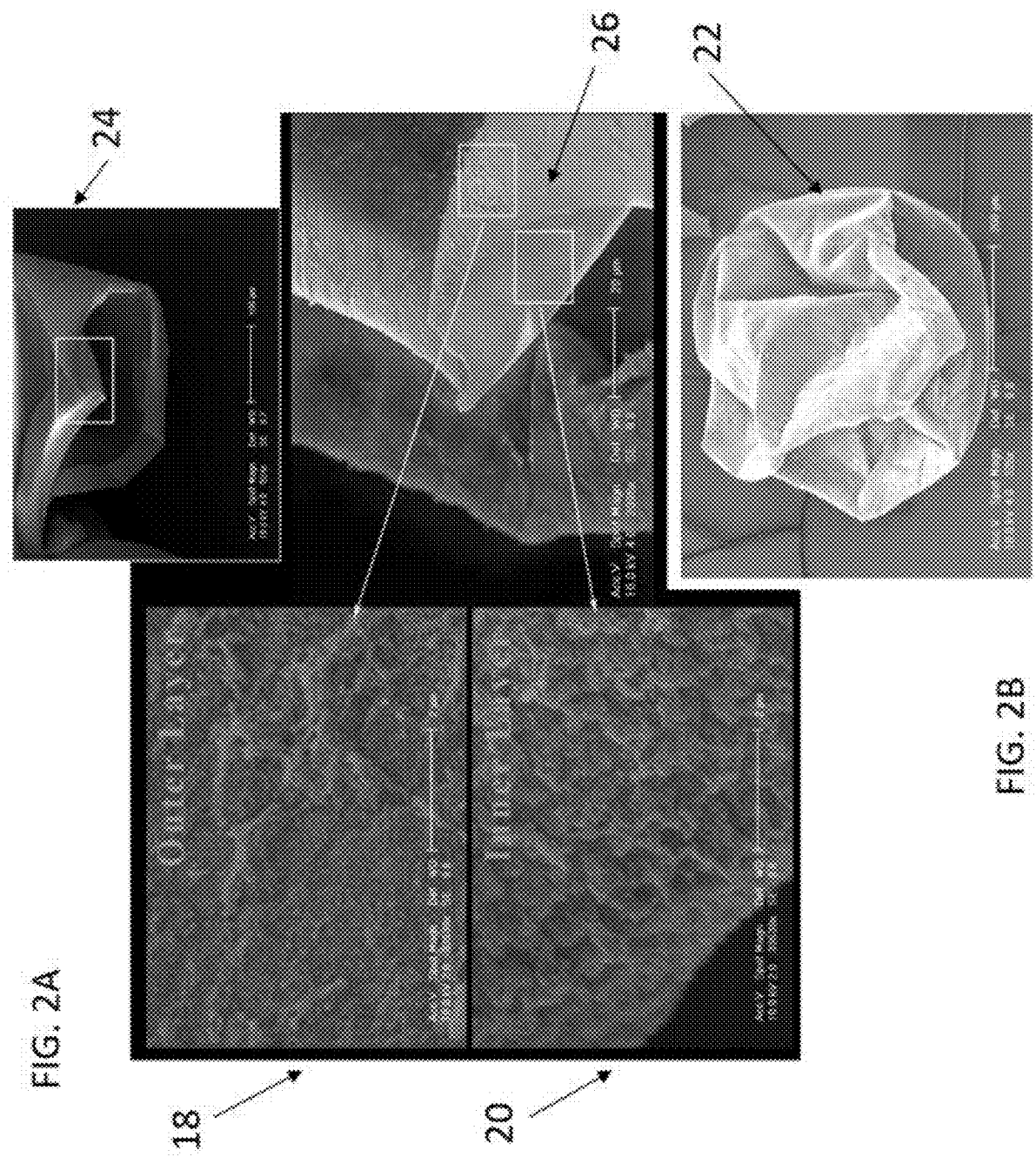

FIG. 3D

IgM Concentration (96 Hours)

| Non-encapsulated Hyb (Supernatant) μg/ml | Encapsulated hybridoma cells (Supernatant) μg/ml | encapsulated hybridoma cells (inside microcapsules) μg/ml | CPS Hyb Total μg/ml |
|---|---|---|---|
| 134.49±15.84 | 134.53± 24.89 | 246.51±2.26 | 380.96±27.15 |
| | Supernatant % | inside microcapsules % | |
| | 35.16±4.03 | 64.84±4.03 | |

ALGINATE MICROCAPSULES FOR CELL AND MOLECULAR THERAPY THAT SECRETE BIOACTIVE IMMUNE MOLECULES

BACKGROUND

Technical Field

The present invention relates to microcapsules and more particularly microcapsules that are selectively permeable for treatment of disease and other applications.

Description of the Related Art

Sodium Alginate (AG) is widely used as a polymeric material to microencapsulate cells. If properly purified, AG is very biocompatible, and permits simple fabrication of microspheres by an easily scalable, rapid gelation process. These microcapsules, for their intrinsic physical chemical properties, usually constitute immunoisolatory shields that inhibit immune recognition of the encapsulated cells by the host's immune system upon transplantation.

SUMMARY

According to an aspect of the present invention, a membrane including a barrier having layers of alginate with different material molar concentrations relative to another material. The layers have a uniform consistency across a thickness of the layers. The thickness is free of laminae and interfaces and forms a single layer morphology that provides permeability for selected molecules.

In another embodiment, a membrane includes a barrier having a plurality of layers of alginate and poly-L-ornithine (PLO) and having a uniform consistency across the layers free of laminae or interfaces to form a single layer morphology that provides permeability for selected molecules.

Another membrane includes a barrier including a plurality of alginate layers and having a uniform consistency across the layers free of laminae or interfaces forming a single layer morphology that provides permeability for selected molecules.

Yet another membrane includes a barrier including a plurality of layers and having a uniform consistency across the layers free of laminae and interfaces forming a single layer morphology that provides permeability for selected materials, wherein the plurality of layers includes successive layers from an inside layer to an outside layer that alternatingly switch a dominate material of each layer in accordance with molar ratios of two constituent materials. The permeability is configured using one or more of layer thickness and the molar ratios of the two constituent materials.

A method for forming a microencapsulation includes forming an alginate bead; coating the bead with a first layer having a first molar concentration of alginate relative to a second material; and coating the first layer with at least one additional layer to form a barrier including a plurality of layers that alternate a dominant material between alginate and the second material in accordance with molar concentration such that the plurality of layers have a uniform consistency across a thickness of the layers, the thickness being free of laminae and interfaces and forming a single layer morphology that provides permeability for selected molecules.

Another method for forming a microencapsulation includes forming a coating with a first poly-L-ornithine (PLO); over-layering the first PLO with a first ultrapurified sodium alginate; coating the first ultrapurified sodium alginate with a second PLO of lesser concentration than the first PLO; de-gelling; and over-layering with a second ultrapurified sodium alginate.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 2A shows an examination of the IgM secreting new microcapsules under scanning electron microscopy (SEM) after mechanical breakage: inner and outer side of the capsular membranes look very homogeneous in accordance with the present embodiments;

FIG. 2B shows IgM secreting intact microcapsules having outer layer homogeneity with coarctation depending on the technique (critical point) used for samples fixation in accordance with the present embodiments;

FIG. 3D shows that the concentration of the IgM in the medium after 96 hours in accordance with the present embodiments;

DETAILED DESCRIPTION OF PREFERRED EMBODIMENTS

Figure 1A:
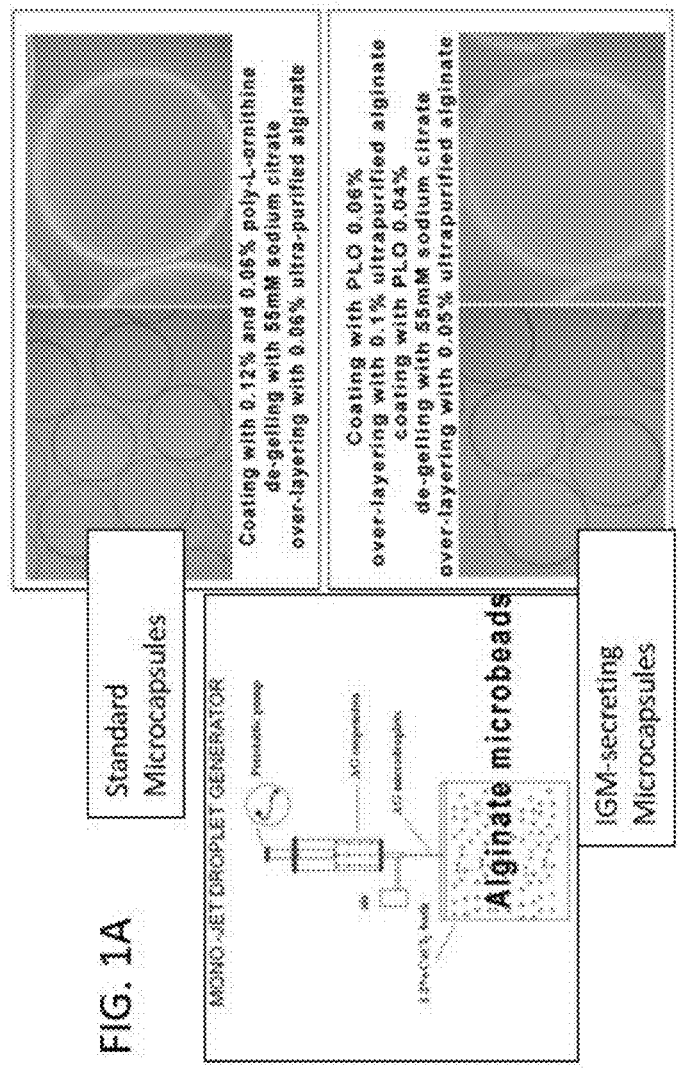
FIG. 1A is a schematic representation of a microcapsules fabrication procedure and comparison of standard with immunoglobulin M (IgM)-secreting microcapsules in terms of composition and an obtained resulting image in accordance with the present embodiments.

In accordance with the present invention, systems, devices and methods are provided for fabrication and use of permeable and semi-permeable microencapsulation membranes. In useful embodiments, alginate microcapsules can be employed for cell and molecular therapy that secrete bioactive molecules. The bioactive molecules can, e.g., provide stimulants to boost cell growth or immunity when the microcapsules are implanted into tissue. The permeable and semi-permeable membrane can be configured to selectively permit passage of different types or sizes of materials or permit the diffusion of the materials through the barrier wall. In some embodiments, the microcapsule can include one or more different materials, some of which can permeate through the barrier and others that cannot.

In one embodiment, the microcapsules include a Sodium Alginate (AG) material. The microcapsules are re-engineered to change their properties to make the microcapsule barrier permeable or semi-permeable to materials. In one instance, materials can be released out of the membrane, and in other instances, materials can be absorbed into the membrane (e.g., growth stimulants, desirable materials, toxins or undesirable materials) depending on the application.

In particularly useful embodiments, immuno-stimulatory monoclonal antibodies (mAbs) are immunoglobulins directed towards surface proteins of immune cells, which result in increased immune responsiveness and prove useful in a number of chronic disorders. Long-term delivery of mAbs may represent a way to stimulate/inhibit the immune system either systemically, or at level of peculiar districts. Since the cells exhibit a natural tendency to aggregate, cell immobilization within microcapsules represents a promising approach to provide optimal shear stress, free growth conditions, etc.

Sodium Alginate (AG) is a polymeric material that can be employed to microencapsulate cells. If properly purified, AG is very biocompatible, and allows simple fabrication of microspheres by an easily scalable, rapid gelation process. These microcapsules, for their intrinsic physical chemical properties, constitute immunoisolatory shields that inhibit immune recognition of the encapsulated cells by a host's immune system upon transplantation. However, to exploit therapeutic potential of mABs derived from microencapsulated hybridoma cells (HY), the capsular membrane has been re-engineered to make it permeable to the secreted immunoglobulins. We prepared the new membranes, based on the same chemistries, but using different coating procedures and reagent molar ratios. While allowing immunoprotection of the enveloped mAbs producing HY, the microcapsules permitted mAb outflow on a regulated delivery kinetics. We completely changed the fabrication procedure of the AG-based microcapsules, to allow immunoglobulin (Ig) delivery out of the capsules while retaining immunoprotection of the enveloped HY cells. Either in vitro, morphological at level of structure and ultra-structure of the new membranes, or Ig secretory kinetics, or in vivo retention of the enveloped hybridoma cells (HY) cells viability are reported.

Use of monoclonal antibodies (mAb) has steadily expanded due to applications to treatment of a number of chronic, autoimmune and neoplastic disorders. Long term delivery of mAb may be a way to stimulate/inhibit immunity systematically or in a peculiar district (in tissue). For instance, long term delivery of mAbs could be useful in the local therapy of rheumatoid arthritis or immune-related diseases of the brain, but also for treatment of systemic autoimmune disorders, such as type 1 diabetes mellitus. The present embodiments can be employed and are contemplated for other uses and the treatment of other diseases as well.

Sodium alginate microcapsules can be designed to contain hybridoma (HY) cells to easily recover the immunoglobulins from the culture medium without excessive costs due to purification procedures and without the risk of not eliminating the hybridoma cells themselves. In particular, microcapsules comprised of sodium alginate (AG), combined or not with polyaminoacidic molecules, such as poly-L-ornithine (PLO), were designed.

Access to microcapsules, filled with hybridoma cells producing mAbs, that unlike the case of the original prototype, are able to cross and outflow the capsular barrier, possibly on regulated delivery kinetics, represents new ways for innovative therapeutic approaches. The challenge to construct such a type of microcapsules was challenging, since the capsules' artificial membrane needs be re-engineered to permit the mAbs outflow.

The AG polymeric material is employed to microencapsulate cells, for technical intrinsic advantages. In fact, if properly purified, AG is very biocompatible, and it allows simple fabrication of microspheres by an easily scaleable, rapid gelation process. AG polymers are linear co-polymers composed of two building units, $\beta$-D-mannuronic (M) and $\alpha$-L-guluronic (G) acids, mainly patterned through the entire molecule in form of MM or GG or MG dimeric blocks. The most relevant characteristics of the alginates are the selective binding to multivalent cations, which allows formation of alginate gel beads. The gel formation always implies a process of specific ion exchange. The affinity of alginates for divalent cations depends on their chemical patterns.

The functional properties of alginates, as an immobilization matrix correlate strongly with composition and dimeric block structure. To obtain well-designed alginate-based beads, the ideal type of alginate, at the ideal concentration, coupled with an ideal concentration of gelling collection solution should be determined. The properties of all alginate-based gel beads include high mechanical and chemical stability, controllable swelling properties, low content of toxic, pyrogenic and immunogenic contaminants, defined pore size, and a narrow pore-size distribution. This may be achieved, at least in part, by selection of and purification of raw alginates, selection and control of the gelling process under appropriate incubation conditions. The presence or absence of chelating agents in the culture medium directly affects the maintenance of mechanical and chemical capsules stability.

In the present disclosure, we describe the preparation of microcapsules, containing HY producing mAbs that are able to cross the microcapsules. To prepare them we used a "high M" alginate, subjected to an ultrapurification procedure that made it endotoxin free (e.g., content not higher than 100 EU/g and preferably less than about 20 EU/g), without proteins and heavy metals. For the gelling process, we selected $Ca^{2+}$. Sodium alginate microcapsules were used in vivo in our laboratories for transplantation of pancreatic islets as well as cells of different nature into recipient with normal immune systems with very positive results.

In these instances, the microcapsules had been overcoated with poly-L-ornithine, an aminoacidic polycation, at appropriate concentrations to create a three-dimensional mesh. The mesh was suitable for titrating membrane's cut-off to reach the desired immunobarrier competence, with special regard to regulation of the free exchange of nutrients and gases, but above all insulin and in general of small-sized molecules, while interdicting passage of humoral or cellular components of the host immune system. In present embodiments, there was a need to ensure adequate shielding of the transplanted cells that did not interfere with the secretion of immunoglobulins. Although this problem has been difficult, it has been dealt with using the same components as the sodium alginate and poly-L-ornithine microcapsules, but combining these molecules in a completely new way. This is the approach that has been followed in this work, in fact multi-layer microcapsules containing mouse hybridoma cells producing a rat IgM have been created, these microcapsules have proved able to contain the hybridoma cells without damaging their viability, these in turn have been able to continuously secrete IgM in vitro and in vivo, without triggering rejection when transplanted in vivo on immunocompetent animal models.

We generated a new prototype of microcapsules, associated with altered diffusion properties, by new chemical engineering methods. These methods ensured immunoprotection of the enveloped hybridoma (HY) cell lines thereby granting for retention of cells viability and function upon graft into allo-/xenogeneic hosts; and permitted outflow of mAb, on a regulated delivery kinetics, through membranes.

Hybridoma cells and cell culture: G3c HY cells were a kind gift of Dr. Jun Shimizu. The cells produce G3c mAb, a rat IgM mAb against murine glucocorticoid-induced tumor necrosis factor-related gene (GITR). Cells are cultured in RPMI medium (GIBCO) with 10% FBS. When purification of IgM mAb was needed, cells were cultured in CD Hybridoma serum-free chemical medium (GIBCO).

AG properties: Powdered alginate is commercially available from Monsanto-Kelco featuring the following properties: Molecular weight=120,000-190,000 kDa; Mannuronic acid (M) and Guluronic acid (G)=M fraction (FM) 61%; G fraction (FG) 39%. It is an "high M" alginate.

Alginate ultrapurification was conducted under GLP conditions, based on patent no. WO 2009093184 A1, incorporated herein by reference. At the end of the process, the obtained alginate solution properties were the following: 1) endotoxin levels, measured by LAL test, <27.8 EU/g (<0.5 EU/ml) (Any level below 100 EU/g in this test is considered endotoxin-free); 2) protein content <0.45%; 3) viscosity 100-300 cps; 4) heavy metal content below the recommended cut off and in particular, e.g., Ca<100 ppm; Cu<40 ppm; Fe<60 ppm; Hg<40 ppb; Mg<40 ppm; Zn<40 ppm; Pb<50 ppm; Si<10 ppm; Mn<10 ppm; Sr<40 ppm; As<100 ppb.

Preparation of standard alginate microcapsules: Microcapsules were prepared, starting from 1.8% high-M sodium alginate solution, produced as previously described. The same physical-chemical parameters were used for all experiments. Briefly, the alginate solution was continuously aspirated, at a fixed flow rate, by a peristaltic pump and extruded through a microdroplet generator; the resulting microdroplets were collected into a solution containing divalent cations which immediately made them turn into gel microbeads. The employed gelling solutions was: 100 mM $CaCl_2$, with this salt (Sigma-Aldrich) being dissolved in sterile NaCl 0.9%. After the gelling, the beads were retrieved, washed twice in saline and sequentially coated with 0.12%, 0.06% poly-L-ornithine (Sigma-Aldrich), de-gelled with 55 mM sodium citrate, and finally over-layered with an outer coat of 0.06% ultra-purified alginate, to obtain biologically acceptable and functionally performing microcapsules. Sterility and viability tests, the latter using ethidium bromide and fluorescein diacetate (Sigma-Aldrich), under fluorescence microscopy, were performed.

Hence, we changed stoichiometric molar ratios (%) of the usual reagents, AG and PLO, employed for microencapsulation, including composition of the capsule's multilayered membrane, by inverting preparation of each layer, from inside to outside. For example, a first layer can include AG with a first concentration of polyaminoacidic molecules (e.g., 0.06% PLO), the next layer includes polyaminoacidic molecules (e.g., PLO) with a first concentration (e.g., 0.1%) of AG, the next layer includes AG with a lower concentration than the first concentration of polyaminoacidic molecules (e.g., 0.04% PLO). This can continue for any number of layers. The layers can be varied in concentration, number and thickness to achieve the desired properties of permeability and direction of permeability for a given application. In a particularly useful embodiment, the molar ratios are inverted for the dominating material in each successive layer. In addition, the concentration of the non-dominate material is reduced for each corresponding material in the layers. The number of layers, their thickness, their molar ratios can all be considered in accordance with an application to provide the desired permeability and direction for materials to pass through the barrier.

In one example, the employed gelling solutions included, e.g., 100 mM $CaCl_2$, (Sigma-Aldrich), dissolved in sterile NaCl 0.9%. After gelling, the beads were retrieved, washed twice in saline and were sequentially coated with, e.g., 0.06% poly-L-ornithine (Sigma-Aldrich), washed twice in saline and over-layered with, e.g., 0.1% ultra-purified alginate, washed twice in saline and coated with a lower concentration (e.g., 0.04%) PLO, washed twice in saline, de-gelled for 3 minutes with 55 mM sodium citrate to liquefy the capsules gel core, and finally washed twice in saline and over-layered with an outer coat of a lower concentration (e.g., 0.05%) ultra-purified alginate. $1.5 \times 10^6$ hybridoma cells per 1 ml of ultra-purified alginate were used; such a AG/cell ratio would avoid formation of empty capsules. The number of layers can vary depending on the application. The cells or molecules added to the encapsulations can be varied and adjusted as needed for specific treatment results.

Transmission electron microscopy (TEM) and Scanning electron microscopy (SEM): Samples were pre-fixed in 2% glutaraldehyde, buffered with 0.2 M Na cacodylate, pH 7.4, for 2 h (hours) at 4° C., rinsed in the same buffer, post-fixed with 2% osmium tetroxide, in the same buffer for 2 h, dehydrated in ethanol graded series, and embedded in epon araldite. To analyze the layers, ultrathin sections were stained with uranyl acetate and lead citrate and examined in TEM 400 T Philips (B Philips) at 60 kV.

SEM: Samples were pre-fixed in 2% glutaraldehyde, buffered with 0.2 M Na cacodylate, pH 7.4, for 2 h at 4° C., rinsed in the same buffer, post-fixed with 2% osmium tetroxide, in the same buffer for 2 h, dehydrated in ethanol graded series, critically point dried and coated with gold palladium. Examination of the samples was conducted under SEM, Philips Scanning Electron Microscope, B Philips, The Nederlands, at 15 Kv.

Purification of IgM mAb: G3C cells were cultured for 14 days in a serum-free chemical medium (GIBCO). G3c-derived IgM mAbs was purified using HiTrap IgM Purification HP column (1 ml size) for affinity purification (GE Healthcare), following the manufacturer instructions. The column allows the purification of a maximum of 5 mg of IgM per sample. Briefly, the IgM mAbs present in the supernatant of the cell culture (150 ml) were concentrated (final volume 1.5 ml) using Amicon ultra-15 columns (Millipore) with a molecular weight cut-off of 100 kDa so that the proteins bigger than 100 kDa were retained. Then, the concentrated supernatant was diluted in 10 ml of ammonium phosphate 1M solution and was loaded on the HiTrap IgM Purification HP column, equilibrated with 5 ml of binding buffer (20 mM sodium phosphate and 1 M ammonium phosphate, pH 7.5); the unbound sample was washed out from the column with 15 ml binding buffer, The IgM mAb were eluted with 12 ml elution buffer (20 mM sodium phosphate, pH 7.5). The buffer containing the IgM mAbs was exchanged with PBS through dialysis, using Slide-A-Lyzer Dialysis Cassette (10.000 MWCO (Thermo Scientific). The purified G3c IgM mAb was quantified using the Bradford method. Considering that the culture medium was synthetic and did not contain serum, the obtained concentration was considered to associate with G3c IgM mAb.

ELISA (Enzyme linked Immunosorbent Assay): We developed an ELISA testing to quantify the level of G3c IgM mAb produced by G3C cells. In brief, we coated the microplate wells with 250 ng of GITR Fc protein (Adipogen) or Fc as control (Adipogen) over 16 h of incubation. After washing out the of protein excess and blocking the plate with the blocking buffer for 30 min, samples (culture medium, dilute 1:4 with PBS and purified IgM mAb as standard) were added; following 16 h incubation, wells were washed and biotin-anti-Rat IgM Ab (5 µg/ml) (BD Pharmingen) was added; after 2 hrs (h) of incubation, the antibody was washed out and a Streptavidin HRP conjugate (dilution 1:1000) (BD Pharmingen) was added. Thirty minutes later, the excess HRP conjugate was washed out and an ABST substrate solution was added. After an appropriate time, the reaction was stopped with SDS 1% solution and the plate was read under Tecan microplate reader (405/600 nm). The purified IgM mAbs were used for reference. Optimization of ELISA was obtained by testing different concentrations (plate coating ranging from 100 to 400 ng of GITR Fc, and biotin-anti-Rat IgM ranging from 1 to 10 ug/ml). ELISA permits a good quantification of IgM within a 10 to 1000 ng range (data not shown).

Histological and immunohistochemical analyses (IHC): For histological and immunohistochemical examination, the samples were fixed in 10% neutral buffered formalin for 24 h at room temperature, dehydrated and paraffin embedded. Paraffin embedded specimens were cut with a rotary microtome. Immunohistochemical analysis was performed on 3.5 µm slides using primary antibodies, specific for rat IgM. Immunohistochemistry relied on the automated Leica BOND system (Leica Biosystems 2 Stem Cells International Newcastle Ltd., UK) on a Leica BOND-III instrument. The slides were counterstained with hematoxylin.

Animals: The encapsulated hybridoma cells were grafted intraperitoneally, into mice upon general anesthesia. $1.5 \times 10^6$ hybridoma cells in 1 ml of microcapsules per mouse were grafted. Mice were sacrificed at 12 days, while the remainders at 30 days of TX. The microcapsules were retrieved by peritoneal lavage with saline and placed in sterile tubes. Upon accurate washing, to discard blood or peritoneal cells, the capsules were re-suspended in complete medium and deposited in culture flasks, at 37° C., 95% air/$CO_2$ for further assessment. Upon 24 h of incubation, microcapsules aliquots were tested for viability, while the remainder capsules were fixed in 10% neutral buffered formalin for immunocytochemical examination.

All immunocompetent mice were housed in the Perugia University Veterinary Service Center in accordance with institution-approved animal care guidelines. All procedures were approved by the University of Perugia Animal Welfare Committee.

RESULTS: Production of hybridoma containing, IgM secreting microcapsules.

Microencapsulation of hybridoma cells involves suspension of the cells in a 1.8% sodium alginate solution at the concentration of $1.5 \times 10^6$ hybridoma cells per 1 ml of ultrapurified alginate. The cells/AG suspension was pumped through an Air-Droplet generator that, by means of an air shears and mechanical pressure, sprays the generated cells/AG microdroplets onto a 1.2% calcium chloride solution. The latter immediately turned the microdroplets into gel micro-beads containing the cells. Up to this point, the production procedure of the new capsules did not differ from the standard microencapsulation process. The new procedure consisted of the following technical steps of coating with PLO and diluted AG.

FIG. 1A shows a schematic representation of microcapsules fabrication procedure and comparison of standard with IgM-secreting microcapsules in terms of composition and obtained results. FIG. 1A depicts the sequential steps involved with the microcapsules preparation. One substantial difference, in comparison with standard alginate microcapsules, lies on the fact that the PLO coatings are differently intertwined with diluted alginate layers. For example, coating with PLO (e.g., 0.06%), over-layering with 0.1% ultrapurified AG, coating with PLO (e.g., 0.04%), de-gelling with 55 mM sodium citrate, over-layering with 0.05% ultrapurified AG. This can be repeated for more layers. This new technique permits access to microcapsules that macroscopically look the same as usual (for example in the mean value of the diameter or in the shape), but, when analyzed in detail, they reveal profound differences.

Figure 1B:
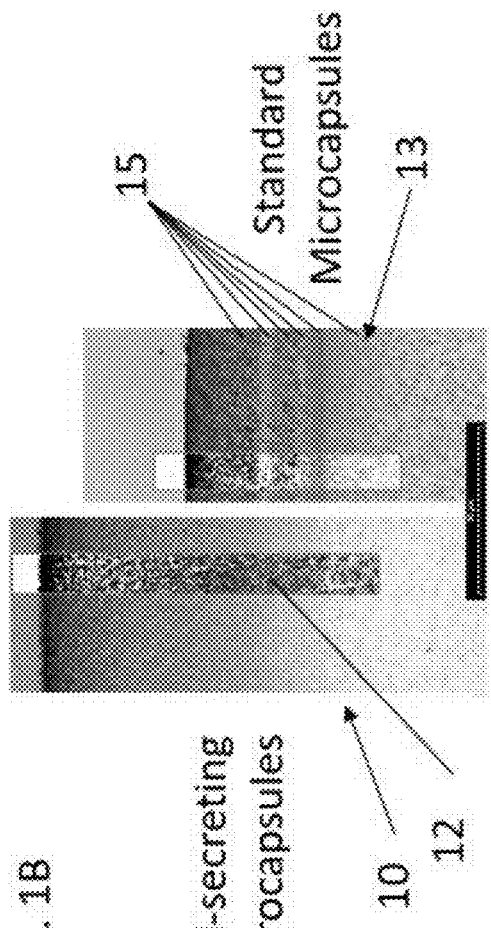
FIG. 1B shows a transmission electron microscopy (TEM) analysis of capsular membranes: the IgM-secreting microcapsules show a wall thickness almost doubling with IgM secreting microcapsules showing no irregular patterns, using osmium precipitation (osmium has a high reflectivity and is employed with TEM to view the consistency in the capsule wall) with the present procedure, the concertation appears to be constant or gradually increasing from the outside to the inside in accordance with the present embodiments.

Referring to FIG. 1B, a membrane (IGM-secreting microcapsules) 10 includes a barrier 12 having a plurality of layers of alginate and poly-L-ornithine (PLO) and having a uniform consistency across the layers free of laminae and interfaces, as shown. The barrier 12 is permeable or semi-permeable and forms a single layer morphology (see FIG. 1B with the barrier 12 shown in cross section) that provides permeability for selected molecules. The single layer morphology functions as a mesh designed to permit selected materials in or out of the microencapsulation (e.g., IgM). The concertation (e.g., osmium) appears to be constant or gradually increase from the outside to the inside of the membrane 10. This low gradient or consistent concentration indicates a single morphological structure. On the contrary, the wall of a standard capsule 13 shows layers 15 in a multi-layered morphology.

Analysis by transmission electron (TEM) and scanning electron microscopy (SEM) of the new microcapsules: Examination under transmission electron microscopy (TEM) was associated with considerable differences at level of the coating layers as compared to the standard microcapsules.

FIG. 1B shows a TEM analysis of capsular membranes with the IgM-secreting microcapsules (10) with a wall thickness almost doubling one of standard microcapsules (13). IgM secreting microcapsules show no irregular patterns, as it appears from osmium precipitation in this procedure. In fact, osmium precipitation appears to gradually increase from the outside to the inside. On the contrary, wall of the standard capsules show a typical multi-layered morphology. FIG. 1B shows that the actual wall thickness was 17 μm as compared to the 10 μm of standard microcapsules.

Moreover, TEM of the new microcapsules showed different membrane's architecture: the gradient layers look homogeneous and continuous, differently from the wall's discontinuous appearance of the standard microcapsules. This seems to reflect different reactivity of osmium with the constituent microcapsules layers in the new versus standard constructs.

FIG. 2A shows an examination of the IgM secreting new microcapsules under a scanning electron microscopy (SEM) after mechanical breakage: an inner layer 20 and outer layer 18 of a capsular membrane 22 is very homogeneous. The capsular membrane is shown magnified in views 24 and 26 of FIG. 2B. The examination of the new microcapsules under SEM showed that the inner side 20 and the outer side 18 of the capsules' membrane. In the exhibited picture (FIG. 2A), the microcapsules had been cut deliberately.

FIG. 2B shows the IgM secreting intact microcapsules 22 with outer layer homogeneity. Coarctation depends on the technique (critical point) used for samples fixation. However, when analyzing the uncut samples, the preparations appear to be free of breakages or inhomogeneous surfaces (FIG. 2B). Hence, the new microcapsules did not show weaker or dented portions, but just even smoother surface areas.

Figure 3A:
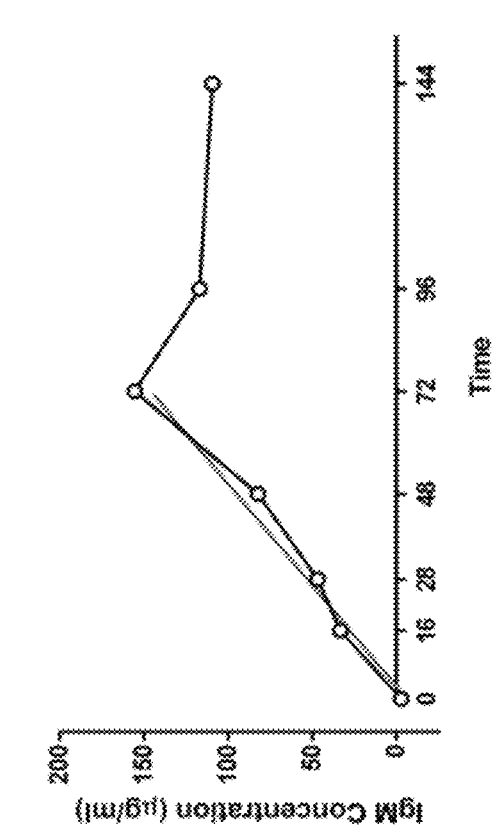
FIG. 3A shows morphological behavior of hybridoma cells before and after microencapsulation where TEM analysis confirms healthy status of the encapsulated cells in accordance with the present embodiments.

FIG. 3A shows the morphological behavior of hybridoma cells before and after microencapsulation. TEM analysis confirms healthy status of the encapsulated cells at different magnifications.

Figure 3C:
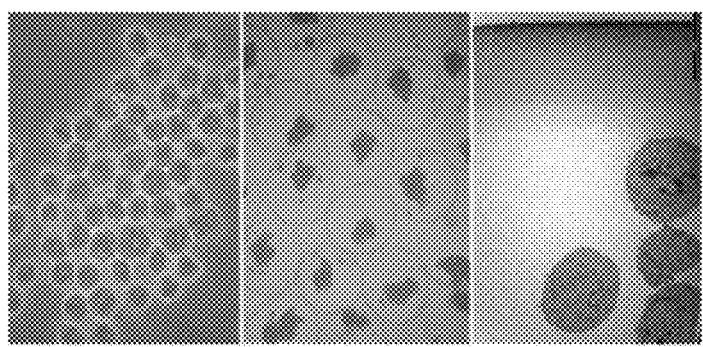
FIG. 3C shows immunoglobulin concentration in the culture medium, increasing linearly, with culture incubation time up to 72 hours, and remaining at a plateau up to 144 hours showing that IgM mAb can permeate out of the new microcapsules in accordance with the present embodiments.
Figure 3B:
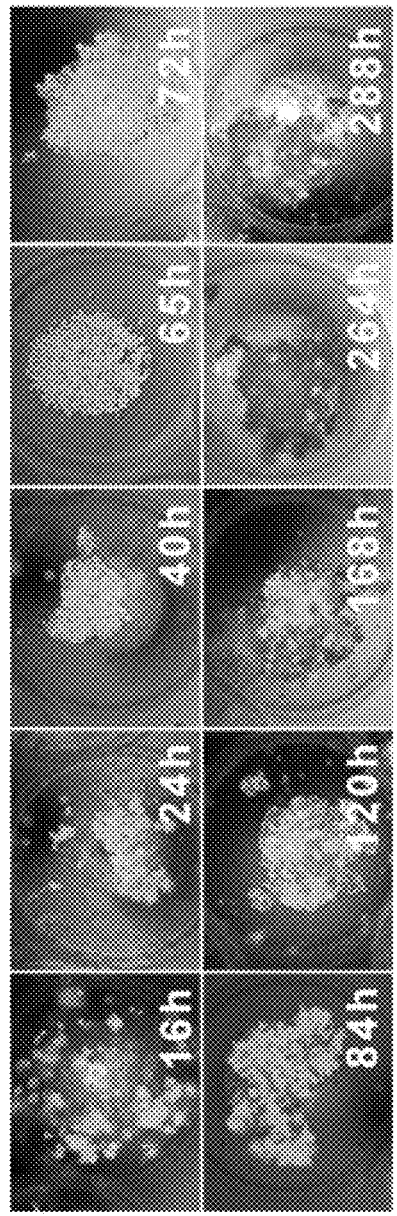
FIG. 3B shows cell viability, at indicated time points, which grow and peak at 95% throughout 84 hours in accordance with the present embodiments.

FIG. 3B shows cell viability, at indicated time points, which grow and peak at 95% throughout 84 hours. FIG. 3C shows immunoglobulin concentration in the culture medium, increasing linearly, with culture incubation time up to 72 hours, and remaining at a plateau up to 144 hours. Hence, IgM mAb can permeate out of the new microcapsules.

Microencapsulation of hybridoma cells does not exert adverse effects on cells. After microencapsulation of hybridoma cells, microcapsules were incubated in the culture medium under standard conditions. FIG. 3A shows morphological behavior of hybridoma cells before microencapsulation and after the microencapsulation procedure. TEM analysis confirms health of these encapsulated cells. At the indicated time, capsules aliquots were taken to test cell viability with the ethidium bromide/fluorescein diacetate test. As shown in FIG. 3B the cells grew and retained viability up to 95% throughout 84 hours. Moreover, most cells were alive until 7 days of culture maintenance and some live cells were detectable also after 12 day culture.

Thus, the hybridoma cells secreting IgM mAbs can be easily enveloped in microcapsules, within a process that does not alter their viability. On the contrary, microencapsulation promotes their growth.

Microencapsulated hybridoma cells produce IgM mAb that can be found outside the capsules. To evaluate the presence of IgM mAb in the secreted IgM in the medium with microcapsules, we employed ELISA. FIG. 3C shows that the immunoglobulin concentration in culture medium increased linearly with increasing culture time for up to 72 hours, demonstrating that IgM can exit from the microcapsules. The secretion decreases and reaches a plateau after 72 hours and up to 144 hours. Then, we tested the concentration of the IgM in the medium with microcapsules. As compared with that in the medium, not-encapsulated hybridoma cells were cultured. FIG. 3D shows that the concentration of the IgM in the medium. After 96 hours, the culture was similar between the microencapsulated and not-microencapsulated hybridoma cells. It is interesting to note that a higher concentration of IgM was found inside hybridoma containing microcapsules, suggesting that the equilibrium between outside and inside the capsule takes a certain time to reach steady state conditions, while the microcapsules might serve for storage of a fraction of the produced IgM mAb.

Microencapsulated hybridoma cells are protected from the graft rejection and survive better in vivo than in vitro. The capsules containing hybridoma cells were transplanted intraperitoneally into immunocompetent animals, to verify their effective ability to protect the incorporated cells from the recipient's immune system. After 3 weeks, the capsules were retrieved from the peritoneum and assessed as far as morphology, viability and presence of IgM mAbs were concerned.

Figures 4A, 4B:
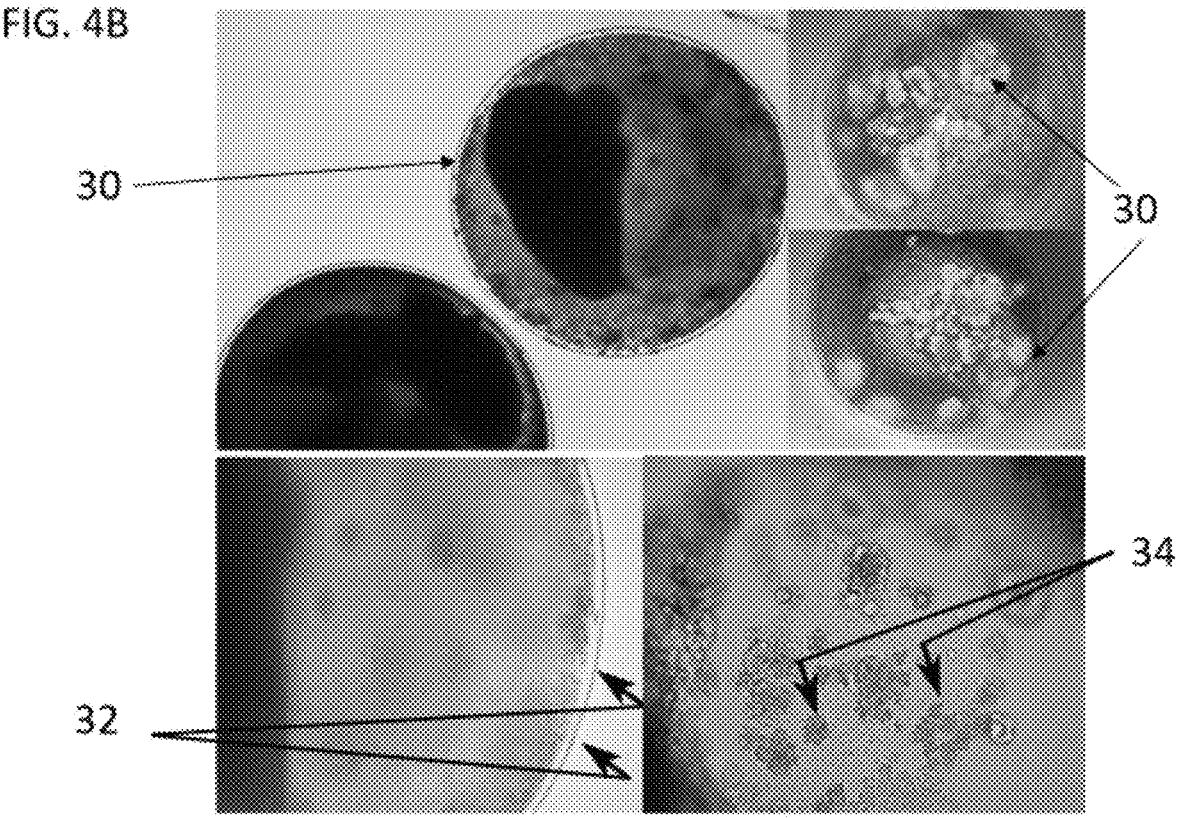
FIG. 4A shows empty capsules retrieved from mice peritoneum 3 weeks post transplantation and showing complete absence of any inflammatory cell reaction in accordance with the present embodiments.
FIG. 4B shows IgM secreting microcapsules retrieved from the peritoneal cavity of mice at 3 weeks post transplantation with the cells showing retention of viability within a visible intact, capsular membrane, where at higher magnification, capsular wall on the left, and IgM precipitates out of the cells (indicated by arrows 34 shown on the right) and HY cells at 3 weeks of microencapsulation in accordance with the present embodiments.

FIG. 4A shows empty capsules (microcapsules) retrieved from mice peritoneum 3 weeks post transplantation; it is evident that there is a complete absence of any inflammatory cell reaction.

In FIG. 4B, IgM secreting microcapsules 30 retrieved from the peritoneal cavity of mice at 3 weeks post transplantation are shown. The cells 30 show retention of viability within a well visible intact, capsular membrane. At higher magnification, a capsular wall 32 on the left of the image, and IgM precipitates out of the cells (indicated by arrows 34) on the right of the image are shown. HY cells at 3 weeks of microencapsulation are shown.

Figure 4C:
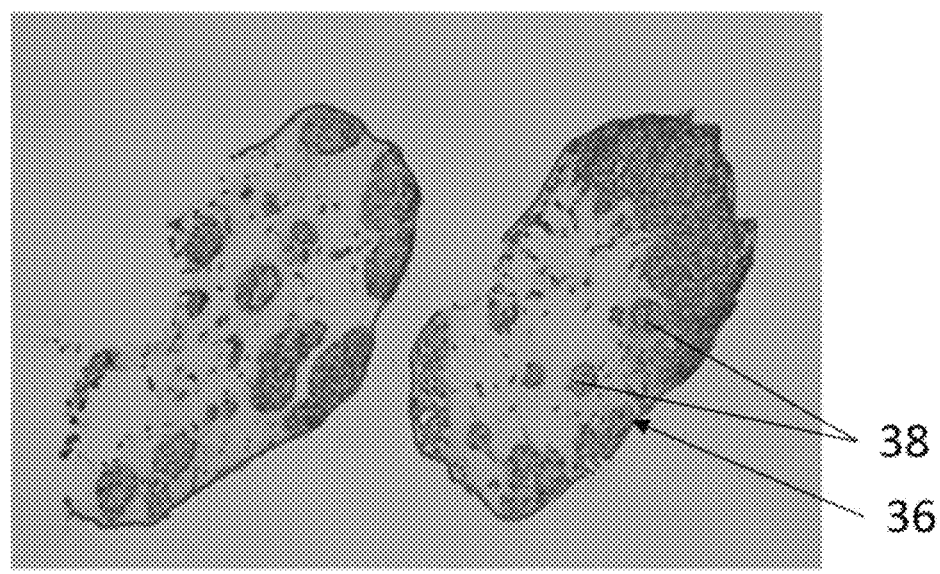
FIG. 4C shows H&E staining: physical integrity of the HY cell clusters within capsules is evident in accordance with the present embodiments.

FIG. 4C shows H&E staining indicating the physical integrity of the HY cell clusters 38 within capsules 36.

Figure 4D:
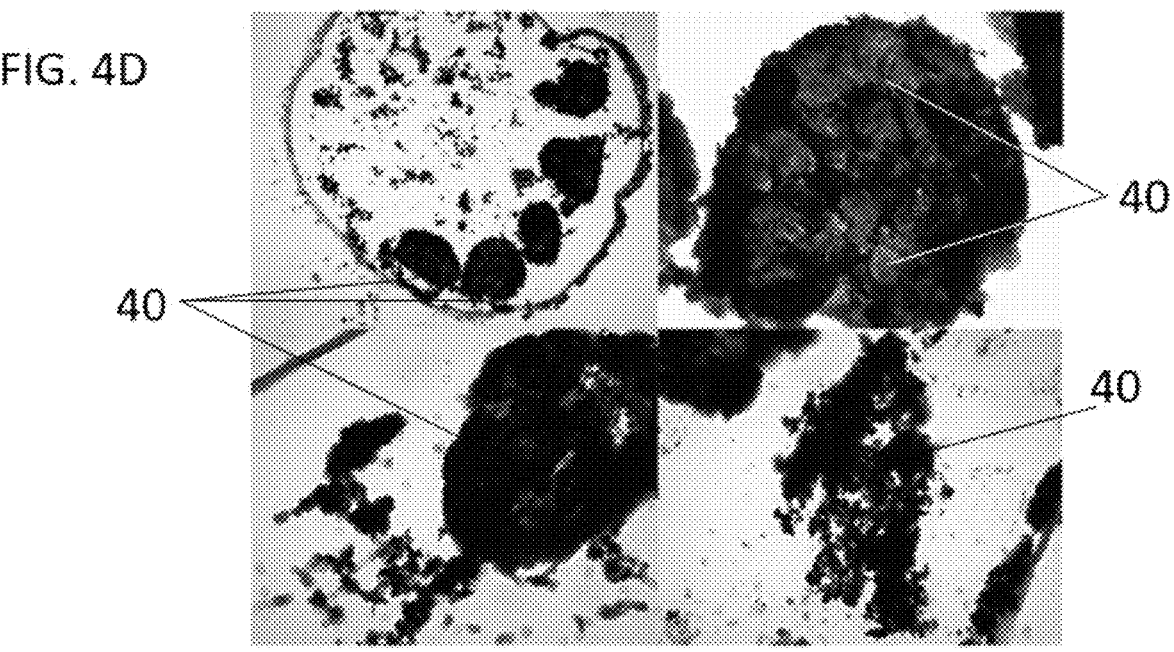
FIG. 4D shows immunocytochemical analysis with positivity for the anti-IgM antibody confirming that the cells are still capable of producing IgM and secrete the same within the capsular environment where they collect in the form of well visible precipitates in accordance with the present embodiments.

FIG. 4D shows an immunocytochemical analysis that indicates positivity for the anti-IgM antibody confirming that the cells are still capable of producing IgM and secretes them within the capsular environment where they collect in the form of well visible precipitates 40.

The new microcapsules did not induce any reaction when transplanted empty into the peritoneum of immunocompetent mice: in fact, their appearance, after recovery, was identical to the pre-graft conditions, with no cellular overgrowth, neither inside the capsule nor outside them (FIG. 4A). Even hybridoma cell-containing microcapsules did elicit any immune reaction. In fact, they appeared intact at the time of recovery and the capsule's wall was clearly detectable (no breakage, dents or, wall irregular patterns) (FIG. 4B). Viability of the encapsulated cells was more than 60% after 3 weeks of transplantation (FIG. 4B) thus higher than one of the encapsulated cells cultured in vitro for over 1 week (FIG. 3B). Cells within microcapsules, in some instances formed aggregates, and color spots were detectable inside the capsules. Immunohistochemical analysis on the retrieved microcapsules showed IgM mAb within the cytoplasm of hybridoma cells demonstrating that cells were still producing these antibodies, and also precipitates within the microcapsules consisting of IgM depots (FIGS. 4C and 4D).

IgG mAbs are used in clinics to treat patients affected by several disorders, such as tumors, inflammatory and autoimmune diseases. A number of preclinical studies evaluated the activity of several mAbs, including some not belonging to IgG isotypes. We describe a new technology to microencapsulate hybridoma cells. Alginate polymers are very stable and useful for these purposes. They have been employed with a great number of cells producing bioactive proteins, such as, e.g., hormones, erythropoietin, angiogenic factors, neurotrophic factors, endostatins, growth factors, cytokines and immunomodulatory agents of mesenchymal arts. Additionally, high biocompatibility of alginate and the benefits associated with cell immobilization systems are some of the advantages. Consequently, it is possible to set up an efficient bioprocess system with alginates with care being taken to use suitable materials, at optimized physical-chemical parameters.

Hybridoma cells, microencapsulated by the present embodiments, are protected from graft rejection when implanted into allo-/xenogeneic hosts, with full retention of cell viability and function including outflow of the synthesized IgM mAbs.

On the basis of our long-standing experience in the field of pancreatic islets but also other cells microencapsulation trials using ultra-purified AGs complexed with stoichiometrically suitable aminoacidic polycations, we have been able to develop a new prototype of AG based microcapsules. We specially worked on changing stoichiometric molar ratios of AG and polyaminoacid so to use the capsule's MWCO with no negative interference on the capsule's immunoisolatory properties. The obtained new capsular microenvironment permitted excellent cell survival and function. As a consequence, IgM mAb produced by the G3C line were stored and slowly released across the modified capsule's membrane.

Hence, the newly formulated microcapsules constitute an efficient drug delivery system. This membrane's flexibility is pivotal to deliver variable amounts of mAbs for different time periods. The new microencapsulation system holds the advantage of coupling well tested basic constituent polymers, whose biocompatibility and physical chemical stability was observed in hundreds of graft trials from small size animals to humans, with a completely new chemical setting. The innovation is associated with clear and unprecedented advantages. AG-based microcapsules can be used to envelop cells and be grafted sub-cutaneously without substantial inflammatory reaction. Our microcapsules are associated with retention of the enveloped cells viability throughout three weeks of the intervention, as shown by achieved results. Microcapsules bioengineering seems to be a straightforward procedure, but many technical skills are needed to form a biocompatible, selective permeable and mechanically resistant artificial membrane. There are many variables of the procedure which need to be complied with, in order to fabricate functionally performing microcapsules. After long work where cell containing microcapsules were grafted in several mammalians, man included, with very promising results, we turned our attention to producing capsules membranes, associated with nominally looser cut-off.

This allowed passage of as heavy molecules as IgM but, by the same token, protected the enveloped xenogeneic G3C from host's immune rejection. Here, while representing a novel approach, for bio-innovative molecules delivery, the new microcapsules overcame the dogma of strict membrane's MWCO tightness to grant for retention of the capsules immunobarrier competence.

The present embodiments can be used or applied in many applications including drug or toxin delivery, cell introduction, remodulation of cellular material, etc. Some examples follow.

In one application, long-term delivery of biologics can employ the microcapsules in accordance with aspects of the invention. Here, the long-term delivery of biologics can include monoclonal antibodies (mAbs), bi-functional antibodies, fusion proteins or other ways to stimulate/inhibit the immune system, at both systemic and local levels. For example, Hybridoma cells can be employed as depicted in FIGS. 1A and 1B.

Figure 5A:
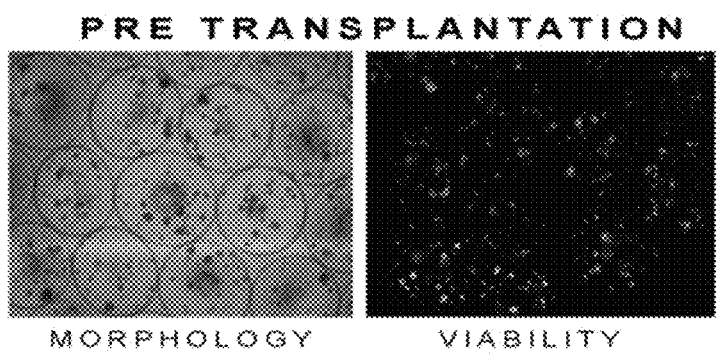
FIG. 5A shows microencapsulated liver cells (e.g., fetal liver differentiated for albumin production) with cell aggregates visible within the capsules and showing cell viability, when encapsulation reaches 98% in accordance with the present embodiments.
Figure 5B:
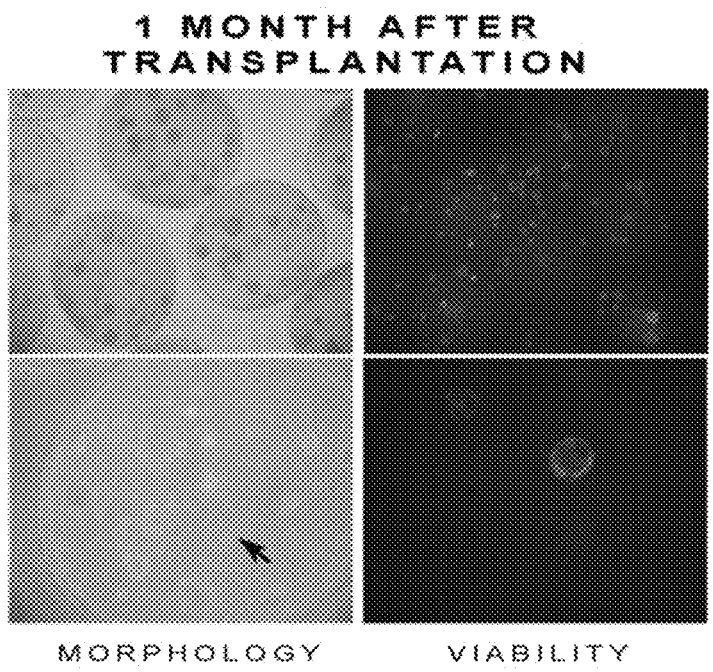
FIG. 5B shows encapsulated liver cells retrieved upon 30 days of graft in the peritoneal cavity of CD1 mice where microcapsules appear intact with no signs of macrophage overgrowth, and the embodied cells look viable and at higher magnification (see arrow) albumin precipitates are visible inside the capsules in accordance with the present embodiments.
Figure 5C:
FIG. 5C shows the liver cells of FIG. 5B, at 60 days after graft in CD1 mice in accordance with the present embodiments.

In other embodiments, microencapsulated liver cells (e.g., fetal liver differentiated for albumin production) can be employed. In FIG. 5A, fetal liver cell aggregates are visible within the capsules before transplanting into tissue. Cell viability, upon encapsulation reaches 98%. In FIG. 5B, the encapsulated liver cells are shown retrieved upon 30 days of graft in the peritoneal cavity of CD1 mice. Microcapsules appear intact with no signs of macrophage overgrowth, and the embodied cells look viable. At higher magnification (indicated by arrow) albumin precipitates are visible inside the capsules. In FIG. 5C, the cells of FIG. 5B are shown at 60 days of graft in CD1 mice.

In other embodiments, microcapsules can contain islets or insulin producing cells (e.g., iPSC) to reverse hyperglycemia in diabetes. In still other embodiments, microencapsulation of therapeutic bispecific antibody-producing cells can be performed, e.g., immunotherapeutic organoids for cancer management, etc.

Permeable and semi-permeable barriers can be employed for other applications as well. While enclosed capsules are contemplated, membrane patches or other structures can also be employed.

It should be understood that the experiments and quantities described throughout this specification are not limiting as other variations are fully contemplated. Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C)

only, or the selection of all three options (A and B and C). This may be extended, as readily apparent by one of ordinary skill in this and related arts, for as many items listed.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Having described preferred embodiments of devices and methods (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A membrane, comprising:
    a barrier including a plurality of layers, each layer having a poly-L-ornithine (PLO) portion and an alginate portion without a defined interface between the two portions, wherein a concentration of PLO molecules in the PLO portion decreases with each successive layer, and wherein barrier permeability is controlled by the PLO concentration in each of the plurality of layers, and
    the barrier, being free of laminae and interfaces, provides permeability for selected molecules.

2. The membrane as recited in claim 1, wherein the PLO molecules form a three-dimensional mesh.

3. The membrane as recited in claim 1, wherein the barrier consists essentially of two layers, wherein the alginate portion in each of the two layers is an ultrapurified alginate.

4. The membrane as recited in claim 1, wherein the barrier forms a bead for long-term delivery of biologics.

5. The membrane as recited in claim 1, wherein the barrier is configured to permit selected molecules to pass out from the barrier and prevent selected molecules from passing in through the barrier.

6. The membrane as recited in claim 1, wherein the barrier is configured to permit by-products of cells contained therein to pass through the barrier while protecting the cells therein from harmful materials outside the barrier.

7. The membrane as recited in claim 1, wherein the barrier is configured to permit permeability of immunoglobulins for regulated release through the barrier.

8. A membrane, comprising:
    a barrier including a plurality of layers and having a uniform consistency across the layers free of laminae and interfaces that provides permeability for selected materials, wherein a first of the plurality of layers includes a first portion of poly-L-ornithine (PLO) with a first PLO concentration and a first portion of alginate, without a defined interface between the first PLO portion and the first alginate portion, and a second of the plurality of layers includes a second portion of poly-L-ornithine (PLO) with a second PLO concentration less than the first PLO concentration, and a second portion of alginate, without a defined interface between the second PLO portion and the second alginate portion, and wherein the permeability is configured using layer thickness and concentrations of the PLO and alginate.

9. The membrane as recited in claim 8, wherein the barrier has a thickness without interfaces between the layers.

10. The membrane as recited in claim 8, wherein the PLO concentration of the PLO portion decreases with each successive layer.

11. The membrane as recited in claim 8, wherein the barrier is configured to permit permeability of immunoglobulins for regulated release through the barrier.

12. A method for forming a microencapsulation, comprising:
    forming an alginate bead;
    forming a first layer having an alginate portion with a first molar concentration of alginate and a first PLO portion with a first molar concentration of PLO; and
    forming a second layer having an alginate portion with a second molar concentration of alginate and a second PLO portion with a second molar concentration of PLO less than the first concentration to form a barrier including a plurality of layers, such that each of the plurality of layers is free of laminae and interfaces, and the barrier provides permeability for selected molecules.

13. The method as recited in claim 12, wherein a molar ratio concentration of PLO decreases with each successive layer.

\* \* \* \* \*